US012797324B2

(12) United States Patent
Jamin et al.

(10) Patent No.: US 12,797,324 B2
(45) Date of Patent: Nov. 17, 2026

(54) LONG-LASTING COSMETIC COMPOSITION

(71) Applicants: CHANEL PARFUMS BEAUTE, Neuilly sur Seine (FR); ROQUETTE FRERES, Lestrem (FR)

(72) Inventors: Julie Jamin, Pantin Cedex (FR); Sarah Sebban Znaty, Pantin Cedex (FR); Flavie Maire-Amiot, Pantin Cedex (FR)

(73) Assignees: CHANEL PARFUMS BEAUTE, Neuilly sur Seine (FR); ROQUETTE FRERES, Lestrem (FR)

( * ) Notice: Subject to any disclaimer, the term of this patent is extended or adjusted under 35 U.S.C. 154(b) by 1132 days.

(21) Appl. No.: 17/599,811

(22) PCT Filed: Mar. 27, 2020

(86) PCT No.: PCT/EP2020/058673
§ 371 (c)(1),
(2) Date: Sep. 29, 2021

(87) PCT Pub. No.: WO2020/201069
PCT Pub. Date: Oct. 8, 2020

(65) Prior Publication Data

US 2022/0192960 A1 Jun. 23, 2022

(30) Foreign Application Priority Data

Mar. 29, 2019 (FR) ..................................... 19 03338

(51) Int. Cl.

| | |
|---|---|
| ***A61K 8/73*** | (2006.01) |
| ***A61K 8/06*** | (2006.01) |
| ***A61K 8/34*** | (2006.01) |
| ***A61K 8/55*** | (2006.01) |
| ***A61K 8/9728*** | (2017.01) |
| ***A61K 8/98*** | (2006.01) |
| ***A61Q 1/04*** | (2006.01) |
| ***A61Q 1/10*** | (2006.01) |

(52) U.S. Cl.
CPC .............. *A61K 8/732* (2013.01); *A61K 8/062* (2013.01); *A61K 8/34* (2013.01); *A61K 8/345* (2013.01); *A61K 8/553* (2013.01); *A61K 8/73* (2013.01); *A61K 8/9728* (2017.08); *A61K 8/987* (2013.01); *A61Q 1/04* (2013.01); *A61Q 1/10* (2013.01)

(58) Field of Classification Search
None
See application file for complete search history.

(56) References Cited

U.S. PATENT DOCUMENTS

| | | | | |
|---|---|---|---|---|
| 8,580,286 B2 * | 11/2013 | Pearlman | A61K 31/573 424/401 |
| 2012/0245234 A1 * | 9/2012 | Le Fur | C08L 5/00 514/777 |
| 2015/0132247 A1 | 5/2015 | Gombart et al. | |

FOREIGN PATENT DOCUMENTS

| | | | | |
|---|---|---|---|---|
| EP | 2937082 A1 | 10/2015 | | |
| FR | 2972924 A1 | 9/2012 | | |
| JP | 2003503316 A | 1/2003 | | |
| JP | 200395908 A | 4/2003 | | |
| JP | 2007511584 A | 5/2007 | | |
| JP | 2011512411 A | 4/2011 | | |
| KR | 20150031238 A2 * | 3/2015 | | |
| KR | 1020150031238 A | 3/2015 | | |
| WO | 2014/155015 A1 | 10/2014 | | |
| WO | WO201415515 A1 * | 10/2014 | | |
| WO | 2016/030842 A1 | 3/2016 | | |
| WO | WO-2018114548 A1 * | 6/2018 | | A61K 8/29 |

OTHER PUBLICATIONS

Daytime Noursihment Cream 2001.*
International Search Report issued on Apr. 29, 2020 in corresponding International Application No. PCT/EP2020/058673; 6 pages.
Anonumous, "Daytime Nourishment Cream", Oct. 10, 2001, 2 pages Retrieved from www.gnpd.com.

* cited by examiner

*Primary Examiner* — Melissa S Mercier
(74) *Attorney, Agent, or Firm* — Maier & Maier, PLLC

(57) ABSTRACT

A cosmetic composition including, in a continuous aqueous phase, at least one leguminous starch having an amylose content greater than or equal to 30%, at least one plasticiser selected from polyols and at least one hydrophilic gelling agent selected from xanthan gum, sclerotium gum, and the mixture thereof. Also, the use of such a composition for forming, on keratinous materials, a sweat and sebum resistant film.

13 Claims, 1 Drawing Sheet

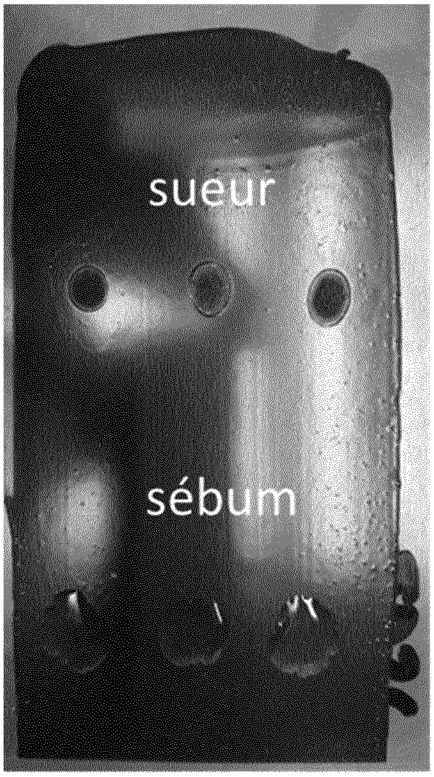
Photo 1
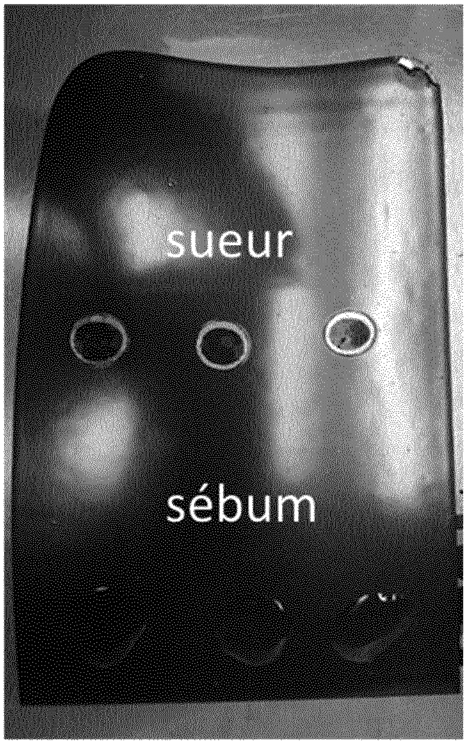
Photo 2

LONG-LASTING COSMETIC COMPOSITION

The object of the present invention is a cosmetic composition comprising, in a continuous aqueous phase, at least one leguminous starch having an amylose content greater than or equal to 30%, at least one plasticiser selected from polyols and at least one hydrophilic gelling agent selected from polysaccharides. The invention also relates to the use of such a composition for forming, on keratinous materials, a sweat and sebum resistant film.

FIELD

Make-up or treatment products for keratinous materials are usually applied in the form of a uniform thin layer. For compositions intended for the make-up of eyelids, for example eyeshadows or eye-liners, it is desirable that the film deposited after the application is resistant to tears, to perspiration and to sebum. Furthermore, it is desirable that the film has a good resistance to the rubbing of fingers.

It is also desirable that the film deposited on the skin has non-transfer properties, that is to say that it does not deposit, even in part, on certain supports with which the skin may come into contact, and particularly clothing.

BACKGROUND

To give these compositions a good staying power on the skin or on the eyelashes, it is known to use film-forming polymers solubilised in a medium consisting of organic solvents.

Film-forming compositions currently use synthetic polymers such as polyvinylpyrrolidone (PVP) or polyvinyl acetate (PVAC). Yet, consumers increasingly look for cosmetic products consisting essentially of natural ingredients or of natural origin, having the minimum of chemical modifications. The elimination of functional synthetic ingredients, or the substitution thereof by ingredients of natural origin, constitutes an important area of development for new cosmetic products. However, the introduction of these new natural ingredients or of natural origin, may be accompanied with a degradation of the properties of the cosmetic product, at its appearance, its application or its cosmetic properties. These insufficient or degraded cosmetic properties are detrimental to the image of the product.

Therefore, there is a need for a cosmetic composition implementing natural ingredients or of natural origin, capable of forming on the keratinous materials a continuous, homogeneous, intense, comfortable, long-lasting in particular sweat and sebum resistant film, that does not migrate and for easy make-up removal by peeling or with water.

SUMMARY

The applicant unexpectedly discovered that by associating a very specific leguminous starch with a gelling system of specific nature, namely selected from polysaccharides, it was possible to produce cosmetic compositions making it possible for forming, on keratinous materials, a continuous, homogeneous, intense, comfortable deposition, having a sufficient resistance to sweat and sebum for procuring long-lasting and non-transfer make-up. Complete elimination of the composition may be carried out by peeling or with water.

Thus, the object of the invention, according to a first aspect, is a cosmetic composition comprising, in a continuous aqueous phase:

- at least one leguminous starch having an amylose content greater than or equal to 30%, preferably between 30% and 75%,
- at least one plasticiser selected from polyols,
- at least one hydrophilic gelling agent selected from xanthan gum, sclerotium gum, and the mixture thereof,
- water.

Another object of the invention, according to a second aspect, is a method for preparing such a composition, comprising:

- mixing the plasticisers with water, and optionally with the emulsifying and/or film-forming agents,
- adding starch while stirring until formation of a gel,
- optionally adding a gelling agent,
- optionally adding a colouring agent,
- optionally adjusting the pH.

Another object of the invention, according to a third aspect, is a make-up or care method for keratinous materials, in particular for the skin, eyelashes, eyebrows or lips, consisting of applying on said keratinous materials, in particular the skin, the eyelashes, the eyebrows or the lips, a composition as described above.

Finally, the object of the invention is the cosmetic use of a composition as described above for forming, on keratinous materials, a sweat and sebum resistant film.

DETAILED DESCRIPTION

Galenic

The composition according to the invention has a continuous aqueous phase. Preferably, it is in the form of an aqueous gel.

Leguminous Starch

The composition according to the invention comprises at least one leguminous starch having an amylose content greater than or equal to 30%, preferably between 30% and 75%.

In particular, the amylose content ranges from 30% to 75%, preferably from 30% to 45%, and more preferably from 35% to 40%. The amylose percentages are expressed in dry weight, in relation to the dry weight of starch, and determined before any subsequent treatment such as a hydrolysis and/or an alkylation of said starch.

The leguminous starch also has a Brookfield viscosity in aqueous dispersion at 25 °C with 20% of dry matter between 10 and 10,000 mPa·s, preferably between 20 and 5,000 mPa·s, more preferably between 50 and 1,000 mPa·s, quite preferably between 75 and 500 mPa·s, and even more preferably at approximately 150 mPa·s.

The Brookfield viscosity in aqueous dispersion at 25 °C with 20% by dry matter weight, is, preferably, between 10 and 10,000 mPa·s, preferably between 20 and 5,000 mPa·s, more preferably between 50 and 1,000 mPa·s, quite preferably between 75 and 500 mPa·s, and even more preferably at approximately 150 mPa·s. These Brookfield viscosity variants may be combined with the amylose content variants.

The viscosity within the meaning of the present invention is a Brookfield viscosity determined by means for example of a Brookfield RDVD-I+ viscometer (Brookfield Engineering Laboratories, INC. Middleboro, MA, USA) by using one of the spindles referenced RV1, RV2, RV3, RV4, RV5, RV6 or RV7 and without using the equipment called "Helipath Stand". The rotation of the spindle is set at 20 revolutions per minute. The spindle, from RV1 to RV7, is selected in such a way that the displayed viscosity value is between 10% and 100% of the total viscosity scale possible with said spindle, as indicated by the manufacturer. To perform this viscosity measurement, 300 ml of an aqueous suspension or aqueous solution at 20% by dry matter weight in starch prepared at 25 °C under mechanical stirring, for example with a deflocculating paddle at 250 rpm during 15 minutes, are placed in a beaker of 400 ml of low form (diameter approximately 7.5 cm). The viscosity value is taken at the end of the 3rd rotation. The measurement is performed by following all of the recommendations given by the manufacturer to obtain a reliable viscosity measurement, for example in the "Operating Instructions, Manual No. M/92-021-M0101, Brookfield Digital Viscometer, Model DV-I+).

"Leguminous" within the meaning of the present invention, means any plant belonging to the families of Caesalpiniaceae, Mimosoideae or Papilionaceae and in particular any plant belonging to the family of Papilionaceae such as for example, the pea, the haricot bean, the bean, the field bean, the lentil, or the lupin.

Thus, the leguminous starch may be selected from pea starches, chickpea starches, bean starches, field bean starches, haricot bean starches, or lentil starches.

According to a preferred embodiment, the leguminous starch is a pea starch, and quite preferably a *Pisum sativum* starch.

Furthermore, the leguminous starch may be a native pre-gelatinised starch, or a chemically modified, optionally pre-gelatinised starch.

The chemically modified leguminous starches may be selected from leguminous starches that have undergone at least one chemical modification, preferably at least two chemical modifications, selected from hydroxyalkylations, carboalkylations, hydrolyses, dextrinifications, succinylation, alkylation, acetylation, cationisation, anionisation. These chemical modifications are modifications for stabilising leguminous starch, in other words for stabilising the viscosity in aqueous solution, in that they make it possible to reduced or eliminate the retrogradation of a gel or of an aqueous solution of said starch.

Thus, the modified leguminous starch implemented within the scope of the present invention may be a hydroxyalkylated, carboxyalkylated, hydrolysed leguminous starch, a dextrin, or a combination thereof.

According to a preferred alternative embodiment, the leguminous starch implemented within the scope of the present invention is a hydrolysed and hydroyalkylated leguminous starch. According to a most preferred alternative, the leguminous starch implemented within the scope of the present invention is a hydrolysed and hydroxypropylated leguminous starch.

"Hydroxypropylated leguminous starch" means within the meaning of the present invention, a leguminous starch substituted by hydroxypropyl groups by any technique known by the person skilled in the art, for example by etherification reaction with propylene oxide. Within the scope of the invention, a hydroxypropylated leguminous starch has, preferably, a hydroxypropyl group content between 0.1 and 20% by dry weight, in relation to the dry weight of hydroxypropylated starch, preferably between 1 and 10% by weight, more preferably between 5 and 9% by weight, and in particular close to 7% by weight. This content is in particular determined by Nuclear Magnetic Resonance spectrometry of the proton, in particular according to the standard EN ISO 11543:2002 F.

"Hydrolysed leguminous starch" means within the meaning of the present invention, a leguminous starch having undergone a hydrolysis operation, that is to say an operation aiming to reduce its average molecular mass. The person skilled in the art knows how to obtain such starches, for example by chemical treatments such as oxidation and acid treatments, or also by enzymatic treatments. The person skilled in the art will naturally adjust the level of hydrolysis, and therefore of fluidification of the starch, depending on the desired viscosity.

Within the scope of the invention, a 'hydrolysed leguminous starch', and optionally pre-gelatinised and/or including other chemical modifications as described above has, preferably, an average molecular weight by weight from 1 to 2,000 kDa, preferably from 10 to 1,000 kDa, quite preferably from 20 to 1,000 kDa, and yet more preferably from 100 to 1,000 kDa. For example, the molecular weight may be from 200 to 800 kDa, from 200 to 500 kDa, from 200 to 400 kDa or also from 200 to 300 kDa. The average molecular weight by weight being determined by HPSEC-MALLS (High-Performance Size-Exclusion Chromatography coupled with on-line Multi-angle Laser Light Scattering).

In particular, the starch after alkylation and hydrolysis will preferably be non granular.

A hydrolysed and hydroxypropylated starch that may preferably be implemented within the scope of the present invention is, for example, commercially available under the trade reference LYCOAT RS 720 or LYCOAT NG 720 by the company Roquette Freres.

Apart from these chemical modifications, the starch according to the invention may have further undergone physical treatments, particularly selected from known operations of gelatinisation, pre-gelatinisation, extrusion, atomisation or drying, treatment operations by microwaves or ultrasounds, of plasticisation or granulation.

In particular, the starch according to the invention may, preferably, be rendered soluble. It may be rendered soluble by any technique known by the person skilled in the art, particularly by heat and/or mechanical treatment, for example by an operation of baking in aqueous medium (pre-gelatinisation), optionally followed by a drying step when obtaining a powder product is desired. The operation aiming to render the starch soluble may absolutely intervene before or after the alkylation and/or hydrolysis of the starch. According to a preferred embodiment, the hydrolysed and hydroxyalkylated starch is pre-gelatinised. Such a starch is commercially available under the trade reference LYCOAT RS 720 by the company Roquette Freres. Alternatively to pre-gelatinisation, it is possible to gelatinise the starch during the preparation of the composition in which it will be implemented.

The hydrolysed and hydroxyalkylated, optionally pre-gelatinised leguminous starch according to the invention may also comprise any other physical and/or chemical modification, from the moment that it does not interfere with the desired properties of said starch. An example of chemical modification is particularly crosslinking.

In particular within the scope of the invention, the starch is present in a dry matter content between 0.1% and 30% by weight, preferably between 1% and 25% by weight, in relation to the total weight of the composition.

When the composition is an eyeshadow, the starch is present in a dry matter content between 20 and 25% by weight, in relation to the total weight of the composition.

Plasticiser

The composition according to the invention also comprises at least one plasticiser selected from polyols.

Polyol means any organic molecule having in its structure at least 2 free hydroxy groups (—OH). These polyols are preferably liquid at ambient temperature (25 °C).

By way of example polyols suitable for implementation in the composition may be selected from propylene glycol, butylene glycol, pentylene glycol, pentanediol, isoprene glycol, neopentyl glycol, glycerol, polyethylene glycols (PEG) having particularly from 4 to 8 ethylene glycol units and/or sorbitol.

Preferably, the polyols are glycerol and sorbitol, more preferably in a mixture with pentylene glycol.

In a particularly preferred embodiment, the composition according to the invention does not comprise plasticisers other than the polyols described above.

According to a particular embodiment, the composition according to the invention comprises 8 to 25% by weight of polyols, preferably 10 to 20% by weight, in relation to the total weight of the composition.

In particular, the composition according to the invention may comprise:

- 5 to 15% by weight of glycerin in relation to the total weight of the composition,
- 3 to 6% by weight of sorbitol in relation to the total weight of the composition, and
- 2 to 3% by weight of pentylene glycol in relation to the total weight of the composition.

Aqueous Phase

The composition according to the invention also comprises an aqueous phase comprising water and optionally, at least one water-soluble solvent other than the polyols described above.

"Water-soluble solvent" designates in the present invention a compound that is liquid at ambient temperature and miscible with water (miscibility in water greater than 50% by weight at 25 °C and atmospheric pressure).

The water-soluble solvents that can be used in the compositions according to the invention may be volatile.

From the water-soluble solvents that may be used in the compositions in accordance with the invention, mention may particularly be made of monoalcohols having from 1 to 5 carbon atoms, in particular from 2 to 5 carbon atoms, such as ethanol and isopropanol, the $C_3$-$C_4$ ketones and the $C_2$-$C_4$ aldehydes.

According to a preferred embodiment, the composition according to the invention comprises at least one monoalcohol having from 1 to 5 carbon atoms, in particular from 2 to 5 carbon atoms, preferably ethanol.

The introduction of a monoalcohol having from 1 to 5 carbon atoms makes it possible to facilitate and accelerate the drying of the film.

According to a particular embodiment, the composition according to the invention comprises 25 to 65% by weight of water, preferably 20 to 60% by weight, in relation to the total weight of the composition.

Hydrophilic Gelling Agent

The composition according to the invention comprises a hydrophilic gelling agent selected from xanthan gum, sclerotium gum, and the mixture thereof.

Xanthan gum and derivatives thereof is for example available under the trade name "Rhéosan" by the company Rhodia Chimie. Sclerotium gum (or sclerotium rolfssii gum), is for its part produced by the Sclerotium rolfissii bacterium, and available under the name Naturajel® by the company DIY Cosmetics or Amigel® by the company Alban Muller Gelling agent means a compound that, in the presence of a solvent, creates more or less strong inter-macromolecular bonds thus inducing a three-dimensional network that freezes said solvent.

In a particular embodiment, the composition according to the invention may also comprise an additional hydrophilic gelling agent other than xanthan gum, sclerotium gum, and the mixture thereof, in particular selected from other polysaccharides, protein derivatives, synthesis or semi-synthesis gels of polyester type, polyacrylates or polymethacrylates and derivatives thereof.

The additional hydrophilic gelling agent may be selected from polysaccharides, protein derivatives, synthesis gels or semi-synthesis gels of polyester type, in particular sulphonic, polyacrylates or polymethacrylates and derivatives thereof.

From the polysaccharides, mention may be made of:

- alga extracts such as agar-agar, carrageenans (iota, kappa, lambda), alginates, in particular of Na or Ca;
- exudates of microorganisms such as gellan gum sold under the trade name "Kelcogel F" by the company NUTRASWEET-KELCO or also iota carrageenan sold under the trade names "Seaspen PF 357" or "Viscarin SD 389" by the company FMC;
- fruit extracts such as pectins;
- gelling agents of animal origin such as protein derivatives, in particular gelatine, of beef or of fish, caseinates;
- polysaccharides possessing a side chain and 6 neutral sugars as described in document FR-A-2759377,
- and mixtures thereof.

From the polyacrylates, mention may be made of: cross-linked acrylic acid, methyl acrylate and 25 OE polyoxyethylene behenyl methacrylate polymers (INCI name: Acrylates/Beheneth-25 Methacrylate Copolymer), such as that sold under the name Novethix L-10 Polymer by the company Lubrizol Advanced Materials, or Rheostyl™ 90 N by Arkema (INCI: Acrylates/Beheneth-25 Methacrylate Copolymer)

The hydrophilic gelling agent according to the invention is selected from xanthan gum, sclerotium gum, and mixtures thereof, for example the mixture marketed under the name Actigum VSX 20 by the company Cargill.

According to a preferred embodiment, the mixture of xanthan gum and of sclerotium gum has a weight ratio (xanthan:sclerotium) between 1:2 to 2:1.

The hydrophilic gelling agent is preferably present in the composition according to the invention at a concentration that may range from 0.1 to 10%, more preferably from 0.2 to 5%, by weight, in relation to the total weight of the composition.

Emulsifying Agent

The composition according to the invention may also comprise an emulsifying agent.

These emulsifying agents may be selected from non-ionic, anionic, cationic, amphoteric surface active agents or also from polymeric surface active agents.

According to one embodiment, the surface active agents that may be used within the scope of the invention are selected from non-ionic surface active agents of HLB between 8 and 20 at 25 °C. Mention may particularly be made of:

- esters and ethers of oses such as the mixture of cetyl stearyl glucoside and of cetyl and stearyl alcohols such as Montanov 68 by Seppic;
- oxyethylene and/or oxypropylene ethers (that may include from 1 to 150 oxyethylene and/or oxypropylene groups) of glycerol;
- oxyethylene and/or oxypropylene ethers (that may include from 1 to 150 oxyethylene and/or oxypropylene groups) of fatty alcohols (particularly of C8-C24, and preferably C12-C18 alcohol) such as the oxyethylene ether of cetearyl alcohol with 30 oxyethylene groups (CTFA name "Ceteareth-30"), the oxyethylene ether of stearyl alcohol with 20 oxyethylene groups (CTFA name "Steareth-20"), the oxyethylene ether of the mixture of C12-C15 fatty alcohols including 7 oxyethylene groups (CTFA name "C12-15 Pareth-7") particularly marketed under the name NEODOL 25-7® by SHELL CHEMICALS fatty acid esters (particularly of C8-C24, and preferably C16-C22 acid) and of polyethylene glycol (that may comprise from 1 to 150 ethylene glycol units) such as PEG-50 stearate and PEG-40 monostearate, marketed under the name MYRJ 52P® by the company ICI UNIQUEMA, or also PEG-30 glyceryl stearate particularly marketed under the name TAGAT S® by the company Evonik GOLDSCHMIDT;

fatty acid esters (particularly of C8-C24, and preferably C16-C22 acid) and of oxyethylene and/or oxypropylene glycerol ethers (that may include from 1 to 150 oxyethylene and/or oxypropylene groups), such as the PEG-200 glyceryl monostearate marketed under the name Simulsol 220 TM® by the company SEPPIC; polyethoxylated glyceryl stearate with 30 ethylene oxide groups such as the product TAGAT S® sold by the company Evonik GOLDSCHMIDT, polyethoxylated glyceryl oleate with 30 ethylene oxide groups such as the product TAGAT O® sold by the company Evonik GOLDSCHMIDT, polyethoxylated glyceryl cocoate with 30 ethylene oxide groups such as the product VARIONIC LI 13® sold by the company SHEREX, polyethoxylated glyceryl isostearate with 30 ethylene oxide groups such as the product TAGAT L® sold by the company Evonik GOLDSCHMIDT and polyethoxylated glyceryl laurate with 30 ethylene oxide groups such as the product TAGAT I® by the company Evonik GOLDSCHMIDT, fatty acid esters (particularly of C8-C24, and preferably C16-C22 acid) and oxyethylene and/or oxypropylene sorbitol ethers (that may include from 1 to 150 oxyethylene and/or oxypropylene groups), such as the polysorbate 20 particularly sold under the name Tween 20® by the company CRODA, the polysorbate 60 particularly sold under the name Tween 60® by the company CRODA, dimethicone copolyol, such as that sold under the name Q2-5220® by the company DOW CORNING, dimethicone copolyol benzoate (FINSOLV SLB 101® and 201® from the company FINTEX), copolymers of propylene oxide and ethylene oxide, also called EO/PO polycondensates lysophospholipids, in particular the lysophosphatidylcholine of following [CHEM1] formula:

[Chem. 1]

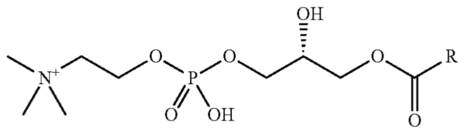

where R is a fatty acid chain, comprising particularly 10 to 25 carbon atoms, preferably 15 to 20. Preferably, the lysophospholipid used in the composition of the invention is from soya seeds. Also preferably, it has the INCI name *Glycine soja* (soybean) seed extract. For example, it is used the mixture of glycerin at 80% by weight and of *Glycine soja* (soybean) seed extract at 20% by weight marketed under the name Lysofix Liquid®;

the emulsifying waxes such as the self-emulsifying wax sold under the name of Polawax NF by Croda, or the beeswax PEG-8 sold under the name of Apifil by Gattefossé, and mixtures thereof.

According to a preferred embodiment, the emulsifying agent of HLB between 8 and 20 is selected from the fatty acid esters and oxyethylene and/or oxypropylene sorbitol ethers, the lysophospholipids, the emulsifying waxes such as the self-emulsifying waxes or the hydrolysed waxes, and mixtures thereof.

The lysophospholipids such as the Lysofix Liquid® make possible a thickening of the composition, thus improving its spreading.

According to one embodiment, the surface active agents that may be used in the composition of the invention are selected from non-ionic surface active agents of HLB less than or equal to 8 at 25 °C. Mention may particularly be made of:

esters and ethers of oses such as sucrose stearate, sucrose cocoate, sorbitan stearate and mixtures thereof such as Arlatone 2121® marketed by the company ICI;

oxyethylene and/or oxypropylene ethers (that may include from 1 to 150 oxyethylene and/or oxypropylene groups) of fatty alcohols (particularly of C8-C24, and preferably C12-C18 alcohol) such as stearyl alcohol oxyethylene ether with 2 oxyethylene groups (CTFA name "Steareth-2");

fatty acid esters (particularly of C8-C24, and preferably C16-C22 acid) and of polyol, particularly of glycerol or of sorbitol, such as glyceryl stearate, such as the product sold under the name TEGIN M® by the company Evonik GOLDSCHMIDT, glyceryl laurate such as the product sold under the name IMWITOR 312® by the company HULS, polyglyceryl-2 stearate, polyglyceryl-2 tristearate, sorbitan tristearate, glyceryl ricinoleate;

lecithins, such as soya lecithins (such as Emulmetik 100 J from Cargill, or Biophilic H from Lucas Meyer);

the cyclomethicone/dimethicone copolyol mixture sold under the name 02-3225C® by the company DOW CORNING.

According to a preferred embodiment, the non-ionic surface active agent of HLB less than or equal to 8 at 25 °C is selected from the fatty acid and polyol esters, preferably polyglyceryl-2 triisostearate such as that marketed under the reference CITHROL PG32IS-LQ by the company Croda (INCI POLYGLYCERYL-3 DIISOSTEARATE).

The composition according to the invention may contain from 0.01 to 30% by weight of emulsifying agent, in relation to the total weight of said composition, preferably from 0.1 to 15% by weight, and more preferably from 0.2 to 13% by weight.

Film-Forming Agent

The composition according to the invention may also comprise an additional film-forming agent other than starch, in particular a film-forming polymer.

From the film-forming polymers that can be used in the compositions of the present invention, mention may be made of synthetic polymers, of radical type or of polycondensate type, polymers of natural origin, and mixtures thereof.

Radical film-forming polymer means a polymer obtained by polymerisation of unsaturated, particularly ethylenic, monomers, each monomer being likely to homopolymerise (contrary to polycondensates).

The film-forming polymers of radical type may particularly be vinyl polymers, or copolymers, particularly acrylic polymers.

The vinyl film-forming polymers may result from the polymerisation of ethylenic unsaturated monomers having at least one acid group and/or esters of these acid monomers and/or amides of these acid monomers.

As acid group carrier monomer, it is possible to use α,β-ethylene unsaturated carboxylic acids such as acrylic acid, methacrylic acid, crotonic acid, maleic acid, itaconic acid. It is preferably used (meth)acrylic acid, itaconic acid and crotonic acid, and more preferably itaconic acid (for example a metallic salt of poly(itaconic acid) such as that marketed under the trade reference REVCARE NE 100S by the company Itaconix).

The acid monomer esters are advantageously selected from the esters of (meth)acrylic acid (also called (meth) acrylates), particularly alkyl (meth)acrylates, in particular of C1-030, preferably C1-C20 alkyl, aryl (meth)acrylates, in particular of C6-C10 aryl, hydroxyalkyl (meth)acrylates, in particular of C2-C6 hydroxyalkyl.

From the alkyl (meth)acrylates, mention may be made of methyl methacrylate, ethyl methacrylate, butyl methacrylate, isobutyl methacrylate, 2 ethyl hexyl methacrylate, lauryl methacrylate, cyclohexyl methacrylate.

From the hydroxyalkyl (meth)acrylates, mention may be made of hydroxyethyl acrylate, 2-hydroxypropyl acrylate, hydroxyethyl methacrylate, 2-hydroxypropyl methacrylate.

From the aryl (meth)acrylates, mention may be made of benzyl acrylate and phenyl acrylate.

The esters of the (meth)acrylic acid particularly preferred are the alkyl (meth)acrylates.

According to the present invention, the alkyl group of esters may be either fluorinated, or perfluorinated, that is to say that all or part of the hydrogen atoms of the alkyl group are substituted by fluorine atoms.

As amides of acid monomers, mention made be made for example of (meth)acrylamides, and particularly N-alkyl (meth)acrylamides, in particular of C2-C12 alkyl. From the N-alkyl (meth)acrylamides, mention may be made of N-ethyl acrylamide, N-t-butyl acrylamide, N-t-octyl acrylamide and N-undecylacrylamide.

The vinyl film-forming polymers may also result from the homopolymerisation or from the copolymerisation of monomers selected from vinyl esters and styrenic monomers. In particular, these monomers may be polymerised with acid monomers and/or esters thereof and/or amides thereof, such as those mentioned above.

As example of vinyl esters, mention may be made of vinyl acetate, vinyl neodecanoate, vinyl pivalate, vinyl benzoate and vinyl tert-butyl benzoate.

As styrene monomers, mention may be made of styrene and alpha-methyl styrene.

From the film-forming polycondensates, mention may be made of polyurethanes, polyesters, polyester amides, polyamides, and epoxy ester resins, polyureas.

The polyurethanes may be selected from anionic, cationic, non-ionic or amphoteric polyurethanes, acrylic polyurethanes, polyurethane-polyvinyl pyrrolidones, polyester-polyurethanes, polyether-polyurethanes, polyureas, polyurea-polyurethanes, and mixtures thereof.

The polyesters may be obtained, in a known manner, by polycondensation of dicarboxylic acids with polyols, particularly diols.

The dicarboxylic may be aliphatic, alicyclic or aromatic. Mention may be made as example of such acids: oxalic acid, malonic acid, dimethylmalonic acid, succinic acid, glutaric acid, adipic acid, pimelic acid, 2,2-dimethylglutamic acid, azelaic acid, suberic acid, sebacic acid, fumaric acid, maleic acid, itaconic acid, phthalic acid, dodecanedioic acid, 1,3-cyclohexane dicarboxylic acid, 1,4-cyclohexane dicarboxylic acid, isophthalic acid, terephthalic acid, 2,5-norbornane dicarboxylic acid, diglycolic acid, thiodipropionic acid, 2,5-naphthalene dicarboxylic acid, 2,6-naphthalene dicarboxylic acid. These dicarboxylic acid monomers may be used alone or in combination of at least two dicarboxylic acid monomers. From these monomers, phthalic acid, isophthalic acid or terephthalic acid is preferably selected.

The diol may be selected from aliphatic, alicyclic or aromatic diols. It is preferably used a diol selected from: ethylene glycol, diethylene glycol, triethylene glycol, 1,3-propane diol, cyclohexane dimethanol, 4-butane diol. As other polyols, it is possible to use glycerol, pentaerythritol, sorbitol or trimethylol propane.

The polyester amides may be obtained in a similar manner to polyesters, by polycondensation of diacides with diamines or amine alcohols. As diamine, it is possible to use ethylenediamine, hexamethylenediamine or meta- or para-phenylenediamine. As amino alcohol, it is possible to use monoethanolamine.

The polyester may further comprise at least one monomer carrying at least one —SO3M group, with M representing a hydrogen atom, an ammonium ion NH4+ or a metal ion, such as for example an ion Na+, Li+, K+, Mg2+, Ca2+, Cu2+, Fe2+, Fe3+. It is particularly possible to use a bifunctional aromatic monomer including such a —SO3M group.

The aromatic core of the bifunctional aromatic monomer further carrying a —SO3M group as described above may be selected for example from benzene, naphthalene, anthracene, diphenyl, oxydiphenyl, sulfonyldiphenyl or methylenediphenyl cores. Mention may be made as example of bifunctional aromatic monomer further carrying a —SO3M group: sulfoisophthalic acid, sulfoterephthalic acid, sulfophthalic acid and 4-sulfonaphthalene-2,7-dicarboxylic acid.

It is preferred to use copolymers based on isophtalate/sulfoisophtalate, and more particularly copolymers obtained by condensation of diethylene glycol, cyclohexanedimethanol, isophtalic acid, sulfoisophtalic acid.

The polymers of natural origin, optionally modified, may be selected from shellac resin, sandarac gum, gum arabic (ACACIA SENEGAL GUM), dammars, elemis, copals, cellulosic polymers, polymers extracted from the fruit of *Caesalpinia spinosa* and/or from the alga *Kappaphycus alvarezii* (such as the product Filmexel® marketed by the company Silab), and mixtures thereof. A natural polymer such as Filmexel® makes it possible particularly to improve the strength of the film obtained from the composition according to the invention.

According to a first embodiment of the invention, the film-forming polymer may be a water-soluble polymer and may then be present in the aqueous continuous phase of the composition according to the invention.

According to a second embodiment, the film-forming polymer may also be present in a composition of the invention in the form of particles in dispersion in an aqueous phase or in a non-aqueous solvent phase, generally known under the name of latex or pseudolatex. The techniques for preparing these dispersions are well known to the person skilled in the art.

As aqueous dispersion of film-forming polymer, it is possible to use the acrylic dispersions sold under the names Neocryl XK-90®, Neocryl A-1070®, Neocryl A-1090®, Neocryl BT-62®, Neocryl A-1079® and Neocryl A-523® by the company AVECIA-NEORESINS, Dow Latex 432® by the company DOW CHEMICAL, Daitosol 5000 AD® or Daitosol 5000 SJ® by the company DAITO KASEY KOGYO; Syntran 5760® by the company Interpolymer, Allianz OPT by the company ROHM & HAAS, the aqueous dispersions of acrylic or styrene/acrylic polymers sold under the brand name JONCRYL® by the company JOHNSON POLYMER or also the aqueous dispersons of polyurethane sold under the names Neorez R-981® and Neorez R-974® by the company AVECIA-NEORESINS, Avalure UR-405®, Avalure UR-410e, Avalure UR-425®, Avalure UR-450®, Sancure 875®, Sancure 861®, Sancure 878® and Sancure 2060® by the company GOODRICH, Impranil 85® by the company BAYER, Aquamere H-1511® by the company HYDROMER; the sulfopolyesters sold under the brand name of Eastman AQ® by the company Eastman Chemical Products, the vinyl dispersions such as Mexomère PAM® from the company CHIMEX and mixtures thereof.

As examples of non-aqueous dispersions of film-forming polymer, mention may be made of the acrylic dispersons in isododecane such as Mexomère PAP® from the company CHIMEX, the dispersions of particles of an ethylenic polymer grafted, preferably acrylic, into a liquid fatty phase, the ethylenic polymer being advantageously dispersed in the absence of additional stabiliser at the surface of the particles as described particularly in the document WO 04/055081.

According to a third embodiment, the film-forming polymer may be a polymer solubilised a liquid fatty phase comprising organic solvents or oils (it is then said that the film-forming polymer is a liposoluble polymer).

By way of example of liposoluble polymer, mention may be made of the copolymers of vinyl ester (the vinyl group being directly bonded to the oxygen atom of the ester group and the vinyl ester having a saturated hydrocarbon radical, linear or branched, from 1 to 19 carbon atoms, bonded to the carbonyl of the ester group) and at least one other monomer, which may be a vinyl ester (different from the vinyl ester already present), an α-olefin (having from 8 to 28 carbon atoms), an alkylvinyl ether (the alkyl group of which comprises 2 to 18 carbon atoms), or an allyl or methallyl ester (having a saturated hydrocarbon radical, linear or branched, from 1 to 19 carbon atoms, bonded to the carbonyl of the ester group).

These copolymers may be crosslinked with the aid of crosslinking agents that may be either of the vinyl type or of the allyl or methallyl type, such as tetraallyloxyethane, divinylbenzene, divinyl octanedioate, divinyl dodecanedioate and divinyl octadecanedioate.

As examples of these copolymers, mention may be made of the copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/octadecene-1, vinyl acetate/dodecene-1, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethyl pentanoate/vinyl laurate, vinyl dimethyl propionate/vinyl stearate, allyl dimethylpropionate/vinyl stearate, vinyl propionate/vinyl stearate, crosslinked with 0.2% divinylbenzene, vinyl dimethyl propionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/octadecene-1 crosslinked with 0.2% divinylbenzene, and allyl propionate/allyl stearate crosslinked with 0.2% divinylbenzene.

As liposoluble film-forming polymers, mention may also be made of liposoluble copolymers, and in particular those resulting from copolymerisation of vinyl esters having from 9 to 22 carbon atoms or alkyl acrylates or methacrylates, the allyl radicals having from 10 to 20 carbon atoms.

Such liposoluble copolymers may be selected from the copolymers of vinyl polystearate, vinyl polystearate crosslinked with the aid of divinylbenzene, diallyl ether or diallyl phthalate, the copolymers of poly(stearyl methacrylate), vinyl polylaurate, poly(lauryl methacrylate), these polymethacrylates being able to be crosslinked with the aid of methylene glycol dimethacrylate or tetraethylene glycol.

The liposoluble copolymers defined above are known and particularly described in the application FR-A-2232303; they may have an average molecular weight ranging from 2,000 to 500,000 and preferably from 4,000 to 200,000.

Mention may also be made of the liposoluble homopolymers, and in particular those resulting from the homopolymerisation of vinyl esters having from 9 to 22 carbon atoms or alkyl acrylates or methacrylates, the alkyl radicals having from 2 to 24 carbon atoms.

As examples of liposoluble homopolymers, mention may particularly be made of: polyvinyl laurate and poly(lauryl methacrylate), these polymethacrylates being able to be crosslinked with the aid of ethylene glycol dimethacrylate or tetraethylene glycol.

As liposoluble film-forming polymers that can be used in the invention, mention may also be made of the polyalkylenes and in particular the C2-C20 alkene copolymers, such as polybutene, alkyl celluloses with a linear or branched alkyl radical, saturated or not, C1 to C8 such as ethyl cellulose and propyl cellulose, the vinyl pyrrolidone (VP) copolymers and particularly the copolymers of vinyl pyrrolidone and alkene, C2 to C40 and better C3 to C20. By way of example of VP copolymer that can be used in the invention, mention may be made of the copolymer of VP/vinyl acetate, VP/ethyl methacrylate, butylated polyvinyl pyrrolidone (PVP), VP/ethyl methacrylate/methacrylic acid, VP/eicosene, VP/hexadecene, VP/triacontene, VP/styrene, VP/acrylic acid/lauryl methacrylate.

Mention may also be made of the silicone resins, generally soluble or swelling in silicone oils, which are crosslinked polyorganosiloxane polymers. The nomenclature of silicone resins are known under the name of "MDTQ", the resin being described depending on the various monomeric siloxane units that it comprises, each of the letters "MDTQ" characterising a type of unit.

By way of examples of polymethylsilsesquioxane resins commercially available, mention may be made of those that are marketed by the company Wacker under the reference Resin MK such as Belsil PMS MK, and by the company SHIN-ETSU under the references KR-220L.

As siloxysilicate resins, mention may be made of the trimethylsiloxysilicate (TMS) resins such as those marketed under the reference SR1000 by the company General Electric or under the reference TMS 803 by the company Wacker. Mention may also be made of the trimethylsiloxysilicate resins marketed in a solvent such as cyclomethicone, sold under the name "KF-7312J" by the company Shin-Etsu, "DOWSIL™ RSN-0749", "DOWSIL™ 593 Fluid" by the company Dow Corning.

Mention may also be made of copolymers of silicone resins such as those cited above with polydimethylsiloxanes, such as the pressure-sensitive adhesive copolymers marketed by the company Dow Corning under the reference BIO-PSA and described in the document U.S. Pat. No. 5,162,410 or also the silicone copolymers resulting from the reaction of a silicone resin, such as those described above, and a diorganosiloxane as described in the document WO 2004/073626.

Finally, mention may be made of the acrylate/polytrimethylsiloxymethacrylate copolymers comprising a dendrimer carbosiloxane structure grafted on a vinyl skeleton commercially available under the references DOW CORNING FA 4002 ID or DOW CORNING FA 4001 CM.

It is also possible to use the silicone polyamides of the polyorganosiloxane type such as those described in the documents U.S. Pat. Nos. 5,874,069, 5,919,441, 6,051,216 and 5,981,680.

According to a preferred embodiment, the additional film-forming polymer is selected from the polymers of natural origin, optionally modified, preferably from the polymers extracted from the fruit of *Caesalpinia spinosa* and/or from the alga *Kappaphycus alvarezii* (such as the product Filmexel® marketed by the company Silab), In a preferred embodiment, the composition according to the invention does not comprise film-forming polymers other than leguminous starch.

Silicone Elastomers

The composition according to the invention may also comprise a silicone elastomer.

The addition of a silicone elastomer particularly makes it possible to limit the fluffing phenomenon likely to occur during the application of the composition according to the invention.

From these, mention may be made of the at least partially crosslinked polymers resulting from the reaction of an organopolysiloxane carrying unsaturated groups, such as vinyl or allyl groups, located at the end or middle of the chain, preferably on a silicon atom, with another reactive silicone compound such as an organohydrogenopolysiloxane These polymers are usually available in gel form in a volatile or non-volatile silicone solvent or in a hydrocarbon solvent. Examples of such elastomers are particularly marketed by the company SHIN ETSU under the trade names KSG-6, KSG-16, KSG-31, KSG-32, KSG-41, KSG-42, KSG-43 and KSG-44, and by the company DOW CORNING under the trade names DOWSIL™ 9040 and DOWSIL™ 9041. Another oily gelling agent consists of a silicone polymer, obtained by self-polymerisation of an organopolysiloxane functionalised by epoxy and hydrosilyl groups, in the presence of a catalyst, which is commercially available from the company GENERAL ELECTRIC under the trade name VELVESIL® 125. Another lipophilic gelling agent consists of a cyclic dimethicone/vinyl dimethicone copolymer such as that marketed by the company JEEN under the trade name JEESILC® PS (of which PS-VH, PS-VHLV, PS-CM, PS-CMLV and PS-DM).

According to a preferred embodiment, the silicone elastomer may be emulsifying, preferably selected from the polyoxyalkylene and polyglycerol silicone elastomers.

As polyoxyalkylene silicone elastomers, mention may be made of those described in the patents brevets U.S. Pat. Nos. 5,236,986, 5,412,004, 5,837,793, 5,811,487.

As polyoxyalkylene silicone elastomers, it is possible to use: those with the INC name PEG-10 Dimethicone/Vinyl dimethicone crosspolymer: such as those marketed under the names "KSG-21", "KSG-20", by Shin Etsu; —those with the INCI name Lauryl PEG-15 Dimethicone/Vinyldimethicone Crosspolymer: such as those marketed under the names "KSG-30" and "KSG-31", KSG-32" (in isododecane), "KSG-33" (in trioctanoine), "KSG-210", "KSG-310" (in a mineral oil), "KSG-320" (in isododecane), "KSG-330", "KSG-340" by the company Shin Etsu.

As polyglycerol silicone elastomers, it is possible to use: —those with the INCI name Dimethicone (and) Dimethicone/Polyglycerin-3 crosspolymer: such as those marketed under the names "KSG-710" by Shin Etsu; those with the INCI name Lauryl Dimethicone/Polyglycerin-3 crosspolymer: such as those marketed under the names "KSG-840" (in squalene) by the company Shin Etsu.

Oils

The composition according to the invention may comprise at least one oil selected from the volatile oils and/or the non-volatile oils, and mixtures thereof.

"Volatile oil" means within the meaning of the invention, an oil likely to evaporate in contact with keratinous fibres within less than one hour, at ambient temperature and atmospheric pressure. The volatile organic solvent or solvents and the volatile oils of the invention are organic solvents and volatile cosmetic oils, liquid at ambient temperature, having a non-zero vapour pressure, at ambient temperature and atmospheric pressure, ranging in particular from 0.13 Pa to 40,000 Pa ($10^{-3}$ at 300 mm of Hg), in particular ranging from 1.3 Pa to 13,000 Pa (0.01 to 100 mm of Hg), and more particularly ranging from 1.3 Pa at 1,300 Pa (0.01 to 10 mm of Hg).

The volatile oil may be hydrocarbon. The hydrocarbon volatile oil may be selected from the hydrocarbon oils having from 7 to 16 carbon atoms. As a hydrocarbon volatile oil having from 7 to 16 carbon atoms, mention may particularly be made of the C8-C16 branched alkanes such as the C8-C16 iso-alkanes (also called isoparaffins), isododecane, isodecane, isohexadecane and for example the oils sold under the trade names Isopars or Permetyls, the C8-C16 branched esters such as iso-hexyl neopentanoate, and mixtures thereof. Preferably, the hydrocarbon volatile oil having from 8 to 16 carbon atoms is selected from isododecane, isodecane, isohexadecane and mixtures thereof, and is particularly isododecane.

The volatile oil may be a volatile linear alkane. According to one embodiment, an alkane suitable for the invention may be a volatile linear alkane comprising from 7 to 14 carbon atoms. Such a volatile linear alkane may advantageously be of vegetable origin. By way of example of alkanes suitable for the invention, mention may be made of the alkanes described in the patent applications of the company Cognis WO 2007/1068371, or WO2008/155059 (mixtures of distinct alkanes and differing by at least one carbon atom). These alkanes are obtained from fatty alcohols, themselves obtained from copra or palm oil. By way of example of linear alkanes suitable for the invention, mention may be made of n-heptane (C7), n-octane (C8), n-nonane (C9), n-decane (010), n-undecane (011), n-dodecane (C12), n-tridecane (C13), n-tetradecane (C14), and mixtures thereof. According to a particular embodiment, the volatile linear alkane is selected from n-nonane, n-undecane, n-dodecane, n-tridecane, n-tetradecane, and mixtures thereof. According to a preferred embodiment, mention may be made of the mixtures of n-undecane (C11) and of n-tridecane (C13) obtained in examples 1 and 2 of the application WO2008/15505 of the company Cognis. Mention may also be made of the mixture of n-undecane (011) and of n-tridecane (C13) marketed by the company BASF under the name of CETIOL ULTIMATE. Mention may also be made of n-dodecane (C12) and of n-tetradecane (C14) sold by Sasol respectively under the references PARAFOL 12-97 and PARAFOL 14-97, as well as mixtures thereof. It may be possible to use the volatile linear alkane alone or preferably a mixture of at least two distinct volatile linear alkanes, differing from each other by a number of carbon atoms n of at least 1, in particular differing from each other by a number of carbon atoms of 1 or 2.

The volatile oil may be a volatile silicone oil such as cyclic polysiloxanes, linear polysiloxanes and mixtures thereof. As linear volatile polysiloxanes, mention may be made of hexamethyldisiloxane, octamethyltrisiloxane, decamethyltetrasiloxane, tetradecamethylhexasiloxane and hexadecamethylheptasiloxane. As cyclic volatile polysiloxanes, mention may be made of hexamethylcyclotrisiloxane, octamethylcyclotetrasiloxane, decamethylcyclopentasiloxane and dodecamethylcyclohexasiloxane.

Alternatively or additionally, the composition produced may comprise at least one fluorinated volatile oil.

"Non-volatile oil" means an oil remaining on the keratinous fibres at ambient temperature and atmospheric pressure for at least a plurality of hours and having in particular a vapour pressure below $10^{-3}$ mm of Hg (0.13 Pa).

The non-volatile oils may, particularly, be selected from hydrocarbon or fluorinated oils and/or non-volatile silicone oils.

As non-volatile hydrocarbon oil, mention may particularly be made of:

- hydrocarbon oils of animal origin,
- hydrocarbon oils of vegetable origin such as C4 to C36, preferably C11-C21 linear alkanes such as plant-derived squalane or Emogreen L15 from SEPPIC (C15-19 alkane), or also such as phytostearyl esters, such as phytostearyl oleate, phytostearyl isostearate and lauroyl/octyldodecyl/phytostearyl glutamate (AJINOMOTO, ELDEW PS203), triglycerides consisting of fatty acid esters and of glycerol, in particular, the fatty acids of which may have chain lengths varying from C4 to C36, and, particularly, from C18 to C36; these oils being able to be linear or branched, saturated or unsaturated; these oils may, particularly, be heptanoic or octanoic triglycerides, shea, alfalfa, poppy, squash, millet, barley, quinoa, rye, candleberry, passion flower oil, shea butter, aloe oil, sweet almond oil, peach kernel oil, peanut oil, argan oil, avocado oil, baobab oil, borage oil, broccoli oil, calendula oil, camelina oil, carrot oil, safflower oil, hemp oil, rapeseed oil, cottonseed oil, copra oil, marrow seed oil, wheatgerm oil, jojoba oil, lily oil, macadamia oil, maize oil, meadowfoam oil, St John's wort oil, monoi oil, hazelnut oil, apricot kernel oil, walnut oil, olive oil, evening primrose oil, palm oil, blackcurrant pip oil, kiwi fruit pip oil, grape seed oil, pistachio oil, squash oil, pumpkin oil, quinoa oil, muscat rose oil, sesame oil, soya oil, sunflower oil, castor oil and watermelon oil, and mixtures thereof, or also caprylic/capric acid triglycerides, such as those sold by the company STEARINERIES DUBOIS or those sold under the names MIGLYOL 810®, 812® and 818® by DYNAMIT NOBEL,
- synthesis ethers having from 10 to 40 carbon atoms;
- synthesis esters, such as the oils of formula R1 COOR2, in which R1 represents a residue of a linear or branched fatty acid comprising 1 to 40 carbon atoms and R2 represents a hydrocarbon chain, particularly, branched containing 1 to 40 carbon atoms provided that R1+R2 is 10. The esters may in particular be selected from alcohol and fatty acid esters, such as for example cetostearyl octanoate, isopropyl alcohol esters such as isopropyl myristate, isopropyl palmitate, ethyl palmitate, 2-ethyl-hexyl palmitate, isopropyl stearate or isostearate, isostearyl isostearate, octyl stearate, hydroxyl esters such as isostearyl lactate, octyl hydrostearate, diisopropyl adipate, heptanoates, and particularly isostearyl heptanoate, octanoates, decanoates or ricinoleates of alcohols or polyalcohols, such as propylene glycol dioctanoate, cetyl octanoate, tridecyl octanoate, 4-diheptanoate and ethyl 2-hexyl palmitate, alkyl benzoate, polyethylene glycol diheptanoate, diethyl propylene glycol 2-hexanoate and mixtures thereof, C12-C15 alcohol benzoates, hexyl laurate, neopentanoic acid esters such as isodecyl neopentanoate, isotridecyl neopentanoate, isostearyl neopentanoate, octyldodecyl neopentanoate, isononanoic acid esters such as isononyl isononanoate, isotridecyl isononanoate, octyl isononanoate, hydroxyl esters such as isostearyl lactate and di-isostearyl malate;
- polyol esters and pentaerythritol esters, such as dipentaerythritol tetrahydroxystearate/tetraisostearatel,
- dimer diol and dimer diacid esters, such as Lusplan DD-DA5® and Lusplan DD-DA7®, marketed by the company NIPPON FINE CHEMICAL and described in the application US 2004-175338,
- dimer diol and dimer diacid copolymers and esters thereof, such as dimer dilinoleyl diol/dimer dilinoleic copolymers and esters thereof, such as for example Plandool-G,
- polyol and dimer diacid copolymers, and esters thereof, such as Hailuscent ISDA,
- fatty alcohols liquid at ambient temperature with a branched and/or unsaturated carbon chain having from 12 to 26 carbon atoms, such as 2-octyldodecanol, isostearyl alcohol, oleic alcohol, 2-hexyldecanol, 2-blatyloctanol and 2-undecylpentadecanol,
- $C_{12}$-$C_{22}$ higher fatty acids, such as oleic acid, linoleic acid and mixtures thereof,
- di-alkyl carbonates, 2-chain alkyls that may be identical or different, such as dicaprylyl carbonate marketed under the name CETIOL CC®, by COGNIS,
- oils with a high molar mass having in particular a molar mass ranging from approximately 400 to approximately 10,000 g/mol, in particular from approximately 650 to approximately 10,000 g/mol, in particular from approximately 750 to approximately 7,500 g/mol, and more particularly varying from approximately 1,000 to approximately 5,000 g/mol,
- silicone oils, such as phenylated silicones such as BELSIL PDM 1000 from the company WACIER (MM=9,000 g/mol). Other non-volatile silicone oils that can be used in the composition according to the invention may be non-volatile polydimethylsiloxanes (PDMS), PDMS including alkyl or alkoxyl groups, pendant and/or at silicone-chain ends, groups each having from 2 to 24 carbon atoms, phenylated silicones, such as phenyl trimethicones, phenyl dimethicones, phenyl trimethylsiloxy diphenylsiloxanes, diphenyl dimethicones, diphenyl methyl diphenyl trisiloxanes and 2-phenylethyl trimethylsiloxysilicates, dimethicones or phenyl trimethicone of viscosity less than or equal to 100 cSt, and mixtures thereof,
- fluorinated oils that can be used in the invention are particularly fluorosilicone oils, fluorinated polyethers and fluorinated silicones as described in the document EP-A-847752.

Waxes

The composition according to the invention may comprise at least one wax.

The wax considered within the scope of the present invention is generally a lipophilic compound, solid at ambient temperature (25 °C), with a reversible solid/liquid state change, having a melting point higher than or equal to 30 °C that may go up to 120 °C.

In particular, the waxes suitable for the invention may have a melting point higher than approximately 45 °C, and in particular higher than 55 °C. The melting point of the wax may be measured with the aid of a differential scanning calorimeter (D.S.C.), for example the calorimeter sold under the name DSC 30 by the company METLER.

The waxes likely to be used in the compositions according to the invention are selected from the solid waxes, deformable or not at ambient temperature, of animal, vegetable, mineral or synthetic origin and mixtures thereof.

The wax may also have a hardness ranging from 0.05 MPa to 30 MPa, and preferably ranging from 6 MPa to 15 MPa. The hardness is determined by measuring the compressive force measured at 20 °C with the aid of a texturometer sold under the name TA-TX2i by the company RHEO, equipped with a 2 mm diameter stainless-steel cylinder moving at a measuring speed of 0.1 mm/s, and penetrating the wax to a penetration depth of 0.3 mm.

In particular, it is possible to use hydrocarbon waxes such as beeswax, lanolin wax, and Chinese insect waxes; rice wax, carnauba wax, candelilla wax, ouricurry wax, alfa wax, cork-fibre wax, sugarcane wax, Japan wax and sumac wax; montan wax, microcrystalline waxes, paraffins and ozokerite; beeswax, jojoba wax, mimosa wax, sunflower wax, polyethylene waxes, waxes obtained by Fisher-Tropsch synthesis and waxy copolymers as well as esters thereof. A mixture of jojoba wax, mimosa wax, sunflower wax is for example marketed under the reference ACTICIRE MP by the company GATTEFOSSE. In particular, the hydrocarbon waxes may be selected from carnauba wax, beeswax, jojoba wax, mimosa wax, sunflower wax and mixtures thereof.

Mention may also be made of the waxes obtained by the catalytic hydrogenation of animal or vegetable waxes having $C_8$-$C_{32}$ linear or branched fatty chains.

From these, mention may particularly be made of hydrogenated jojoba oil, hydrogenated sunflower oil, hydrogenated castor oil, hydrogenated copra oil and hydrogenated lanolin oil, di-(trimethylol-1,1,1 propane) tetrastearate sold under the name "HEST 2T-4S" by the company HETERENE, and di-(trimethylol-1,1,1 propane) tetrabehenate sold under the name HEST 2T-4B by the company HETERENE.

It is also possible to use the waxes obtained by transesterification and hydrogenation of vegetable oils, such as castor or olive oil, such as the waxes sold under the names Phytowax Castor 16L64® and 22L73® and Phytowax Olive 18L57 by the company SOPHIM. Such waxes are described in the application FR-A-2792190.

It is also possible to use silicone waxes, which may advantageously be substituted polysiloxanes, preferably with a low melting point. These silicone waxes are known or may be prepared according to known methods. From the commercial silicone waxes of this type, mention may particularly be made of those sold under the names Abilwax 9800, 9801 or 9810 (GOLDSCHMIDT), KF910 and KF7002 (SHIN ETSU), or 176-1118-3 and 176-11481 (GENERAL ELECTRIC), alkyl- or alkoxydimethicones such as the following commercial products: Abilwax 2428. 2434 and 2440 (GOLDSCHMIDT), or VP 1622 and VP 1621 (WACKER), as well as (C20-C60) alkyldimethicones, in particular (C30-C45) alkyldimethicones such as the silicone wax sold under the name SF-1642 by the company GE-Bayer Silicones.

It is also possible to use hydrocarbon waxes modified by silicone or fluorinated groups such as for example: siliconyl candelilla, siliconyl beeswax and Fluorobeeswax from Koster Keunen.

The waxes may also be selected from fluorinated waxes.

According to a particular embodiment, the compositions according to the invention may comprise at least one so-called sticky wax. As sticky wax, it is possible to use a C20-C40 alkyl(hydroxystearyloxy) stearate (the alkyl group comprising 20 to 40 carbon atoms), alone or in a mixture, in particular a C20-C40 alkyl 12-(12'-hydroxystearyloxy) stearate. Such a wax is particularly sold under the names "Kester Wax K 82 Pe" and "Kester Wax K 80 Pe" by the company KOSTER KEUNEN.

According to a preferred embodiment, the waxes are selected from hydrocarbon waxes, preferably selected from carnauba wax, beeswax, jojoba wax, mimosa wax, sunflower wax, and mixtures thereof.

Lipophilic Gelling Agents

Another type of lipophilic gelling agent consists of styrene and olefin copolymers such as ethylene, propylene and/or butylene, optionally associated with silicone or hydrocarbon solvents, as described in particular in the application WO 98/38981 and in the U.S. Pat. No. 6,309,629. They comprise particularly the gelling agents based on sequenced terpolymers available from the company PENRECO under the trade name VERSAGEL®. Another type of lipophilic gelling agent consists of polymers such as those identified by the INCI name polyamide-3 and in particular the polymers SYLVACLEAR® AF 1900V and PA 1200V available from the company ARIZONA CHEMICAL as well as those identified by the INCI name "Ethylenediamine/Hydrogenated Dimer Dilinoleate Copolymer Bis-Di-C14-18 Alkyl Amide" and available for example under the trade name SYLVACLEAR® A200V or SYLVACLEAR® A2614V from the company ARIZONA CHEMICAL. The lipophilic gelling agent may alternatively be a bentone or a hydrophobic modified hectorite.

Colouring Agent

The composition according to the invention may also comprise a colouring agent selected from soluble, preferably water-soluble, pigments, nacres, colorants.

According to a preferred embodiment, the colouring agent is selected from pigments and/or nacres.

By "pigments", it should be understood white or coloured particles, mineral or organic, insoluble in an aqueous medium, intended to colour and/or opacify the composition and/or the resulting film.

The pigments may be white or coloured, mineral and/or organic.

The pigment may be an organic pigment. Organic pigment means any pigment that meets the definition in the Ullmann encyclopaedia in the organic pigment chapter. The organic pigment may particularly be selected from the compounds of nitroso, nitro, azo, xanthene, quinolene, anthraquinone or phthalocyanine, of the metallic complex type, isoindolinone, isoindoline, quinacridone, perinone, perylene, dicetopyrrolopyrrole, thioindigo, dioxazine, triphenylmethane or quinophthalone.

The organic pigment or pigments may be selected for example from carmine, carbon black, aniline black, melanin, azo yellow, quinacridone, phtalocyanine blue, sorgho red, the blue pigments coded in the Colour Index under the references C1 42090, 69800, 69825, 73000, 74100, 74160, the yellow pigments coded in the Colour Index under the references CI 11680, 11710, 15985, 19140, 20040, 21100, 21108, 47000, 47005, the green pigments coded in the Colour Index under the references CI 61565, 61570, 74260, the orange pigments coded in the Colour Index under the references CI11725, 15510,45370, 71105, the red pigments coded in the Colour Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, 75470, the pigments obtained by oxidative polymerisation of indolic, phenolic derivatives as described in the patent FR 2 679 771.

These pigments may also be in the form of composite pigments as described in the patent EP 1 184 426. These composite pigments may particularly consist of particles including an inorganic core covered at least partially with one organic pigment and at least one binder ensuring the fixing of the organic pigments on the core.

The pigment may also be a lacquer. Lacquer means insoluble colorants adsorbed on insoluble particles, the whole thus obtained remaining insoluble during the use. By way of example of lacquers, mention may be made of the product known under the following name: D & C Red 7 (CI 15 850:1).

The pigment may be a mineral pigment. Mineral pigment means any pigment that meets the definition of the Ullmann encyclopedia in the inorganic pigment chapter. Mention may be made, from the mineral pigments useful in the present invention, of zirconium or cerium oxides, as well as of oxides of zinc, iron (black, yellow or red) or chromium, manganese violet, ultramarine blue, chromium hydrate and ferric blue, titanium dioxide, metallic powders such as aluminium powder and copper powder. The following mineral pigments may also be used: $Ta_2O_5$, $Ti_3O_5$, $Ti_2O_3$, TiO, $ZrO_2$ in a mixture with $TiCO_2$, $ZrO_2$, $Nb_2O_5$, $CeO_2$, ZnS.

The size of the pigment useful within the scope of the present invention is generally between 10 nm and 10 μm, preferably between 20 nm and 5 μm, and more preferably between 30 nm and 1 μm.

The colouring agent may also be a soluble, preferably water-soluble, colorant.

From the water-soluble colorants, mention may be made of cochineal carmine or the products known under the following names: D & C Red 21 (CI 45 380), D & C Orange 5 (CI 45 370), D & C Red 27 (CI 45 410), D & C Orange 10 (0145 425), D & C Red 3 (0145 430), D & C Red 4 (0115 510), D & C Red 33 (01 17 200), D & C Yellow 5 (0119 140), D & C Yellow 6 (0115 985). D & C Green (CI 61 570), D & C Yellow 1 O (CI 77 002), D & C Green 3 (CI 42 053), D & C Blue 1 (CI 42 090).

The nacres may be selected from those conventionally present in make-up products, such as mica/titanium dioxide. Alternatively, this may concern nacres based on mica/silica/titanium dioxide, based on synthetic fluorphlogopite/titanium dioxide (SUNSHINE® from MAPRECOS), calcium sodium borosilicate/titanium dioxide (REFLECKS® from 'ENGELHARD) or calcium aluminium borosilicate/silica/titanium dioxide (RONASTAR® from MERCK).

The composition according to the invention may comprise 0.0001 to 30% by weight of colouring agent, preferably 0.001 to 20% by weight, and more preferably 0.002 to 15% by weight, in relation to the total weight of the composition according to the invention.

Fillers

The composition according to the invention may also comprise at least one filler. These fillers are used particularly to modify the rheology or the texture of the composition.

The fillers may be mineral or organic of any form, platelets, spherical or oblong, regardless of the crystallographic shape (for example leaf, cubic, hexagonal, orthorhombic, etc.). Mention may be made of talc, mica, silica, the silica surface treated by a hydrophobic agent, kaolin, polyamide powders (Nylon®) (Orgasol® from Atochem), poly-β-alanine and polyethylene powders, tetrafluoroethylene polymer powders (Teflon®), lauroyl lysine, starch, boron nitride, hollow polymer microspheres such those of polyvinylidene chloride/acrylonitrile such as Expancel® (Nobel Industrie), acrylic acid copolymers (Polytrap<®> from the company Dow Corning) and silicon resin microbeads (Tospearls® from Toshiba, for example), elastomer polyorganosiloxane particles, precipitated calcium carbonate and magnesium hydra-carbonate, hydroxyapatite, hollow silica microspheres (Silica Beads® from Maprecos), glass or ceramic microcapsules, metallic soaps derived from carboxylic organic acids having from 8 to 22 carbon atoms, preferably from 12 to 18 carbon atoms, for example lithium or magnesium zinc stearate, zinc laurate, magnesium myristate.

Cosmetic Active Agent

The composition according to the invention may also comprise at least one cosmetic active agent, which may be selected in the group consisting of vitamins, antioxidants, hydrating agents, antipollution agents, keratolytic agents, astringents, anti-inflammatories, whitening agents, self-tanning agents and agents promoting microcirculation.

Examples of vitamins include vitamins A, B1, B2, B6, C and E and derivatives thereof, pantothenic acid and derivatives thereof and biotin.

Examples of antioxidants include ascorbic acid and derivatives thereof such as ascorbyl palmitate, ascorbyl tetraisopalmitate, ascorbyl glucoside, magnesium ascorbyl phosphate, sodium ascorbyl phosphate and ascorbyl sorbate; tocopherol and derivatives thereof, such as tocopherol acetate, tocopherol sorbate and other tocopherol esters; BHT and BHA; gallic acid esters, phosphoric acid, citric acid, maleic acid, malonic acid, succinic acid, fumaric acid, cephalin, hexametaphosphate, phytic acid, and plant extracts, for example *Zingiber Officinale* (ginger) roots such as Blue Malagasy Ginger marketed by the company BIOLANDES, *Chondrus crispus, Rhodiola, Thermus thermophilus*, mate leaf, oak wood, Kayu Rapet bark, sakura leaves and ylang ylang leaves.

Examples of hydrating agents include polyethylene glycol, propylene glycol, dipropylene glycol, glycerin, butylene glycol, xylitol, sorbitol, maltitol, mucopolysaccharides such as chondroitin sulphuric acid, hyaluronic acid with high and low molecular weights or hyaluronic acid potentialised by a silanol derivative such as the active agent Epidermosil® marketed by the company Exymol, and mucoitinsulfuric acid; caronic acid, atelocollagen; chlorestearyl-12-hydroxystearate, biliary salts, a principal component of NHF (natural hydration factor) such as a pyrrolidone carboxylic acid salt and a lactic acid salt, an amino acid analogue such as urea, cysteine and serine; a short-chain soluble collagen, PPG diglycerins, homo- and copolymers of 2-methacryloyloxyethylphosphonylcholine such as Lipidure HM and Lipidure PBM from NOF; allantoin; glycerin derivatives such as PEG/PPG/polybutylene Glycol-8/5/3 glycerin from NOF sold under the trade name Wilbride®S753 or glycerylpolymethacrylate from Sederma sold under the trade name Lubragel®MS; the trimethylglycine sold under the trade name Aminocoat® by the company Ashahi Kasei Chemicals and various extracts of plants such as extracts of *Castanea sativa*, hydrolysed hazelnut proteins, polysaccharides of *Polianthes tuberosa, Argania spinosa* kernel oil and the extracts of nacre containing a conchiolin that are sold particularly by the company Maruzen (Japan) under the trade name Pearl Extract®.

Other examples of hydrating agents include the compounds stimulating the expression of the matriptase MT/SP1, such as a carob pulp extract, as well as the agents stimulating the expression of CERT, ARNT2 or FN3K or FN3K RP; the agents increasing the proliferation or the differentiation of keratinocytes, either directly, or indirectly by stimulating for example the production of β-endorphins, such as the extracts of *Thermus thermophilus* or of husks of *Theobroma cacao* beans, the water-soluble extracts of maize, the peptide extracts of *Voandzeia subterranea* and niacinamide; epidermal lipids and the agents increasing the synthesis of epidermal lipids, either directly, or by stimulating certain β-glucosidases that modulate the deglycosylation of lipid precursors such as glucosylceramide into ceramides, such as phospholipids, ceramides, lupin protein hydrolysates and dihydrojasmonic acid derivatives.

Examples of antipollution agents include the extract of Moringa pterygosperma seeds (for example Purisoft® from LSN); the extract of shea butter (for example Detoxyl® from Silab), a mixture of extract of ivy, phytic acid and sunflower seed extract (for example Osmopur® from Sederma).

Examples of keratolytic agents include α-hydroxy acids (for example glycolic, lactic, citric, malic, mandelic or tartric acids) and β-hydroxy acids (for example salicylic acid), and esters thereof, such as the C12-13 alkyl lactates, and the extracts of plants containing these hydroxy acids, such as extracts of *Hibiscus sabdriffa*.

Examples of astringents include hamamelis extracts.

Examples of anti-inflammatory agents include bisabolol, allantoin, tranexamic acid, zinc oxide, sulphur oxide and derivatives thereof, chondroitin sulphate, glycyrrhizinic acid and derivatives thereof such as glycyrrhizinates.

Examples of whitening agents include arbutin and derivatives thereof, ferulic acid (such as Cytovector®: water, glycol, lecithin, ferulic acid, hydroxyethylcellulose, marketed by BASF) and derivatives thereof, kojic acid, resorcinol, lipoic acid and derivatives thereof such as resveratrol diacetate monolipoate as described in the patent application WO2006134282, ellargic acid, leucodopachrome and derivatives thereof, vitamin B3, linoleic acid and derivatives thereof, ceramides and homologues thereof, a peptide as described in the patent application WO2009010356, a bioprecursor as described in the patent application WO2006134282 or a tranexamate salt such as the tranexamate cetylic hydrochloride salt, a liquorice extract (*Glycyrrhiza glabra* extract), which is sold particularly by the company Maruzen under the trade name Licorice Extract®, a whitening agent also having an antioxidant effect, such as the vitamin C compounds, including ascorbate salts, ascorbyl esters of fatty acids or of sorbic acid, and other ascorbic acid derivatives, for example ascorbyl phosphates, such as magnesium ascorbyl phosphate and sodium ascorbyl phosphate, or the saccharide esters of ascorbic acid, which include, for example, ascorbyl-2-glucoside, 2-O-alpha-D-glucopyranosyl L-ascorbate, or 6-O-beta-D-galactopyranosyl L-ascorbate. An active agent of this type is sold in particular by the company DKSH under the trade name Ascorbyl Glucoside®.

An example of self-tanning agent is DHA.

Examples of agents promoting microcirculation include a lupin extract (such as Eclaline® from Silab), butcher's broom, horse chestnut, ivy, ginseng or melilot, caffeine, nicotinate and derivatives thereof, an extract of *Corallina officinalis* alga such as that marketed by CODIF; and mixtures thereof. These active agents on skin microcirculation may be used in order to prevent the complexion becoming dull and/or to improve complexion homogenisation and shine.

The composition according to the invention may comprise 0.0001 to 10% by weight of cosmetic active agent, preferably 0.001 to 5% by weight, and more preferably 0.002 to 1% by weight, in relation to the total weight of the composition according to the invention.

Additives

The composition according to the invention may comprise other ingredients so long as they do not interfere with the desired properties of the composition/of the emulsion of the foundation base. These other ingredients may for example be preservatives, pH adjusters such as citric acid or arginine, antimicrobial agents, perfumes, sun filters, and mixtures thereof.

Preparation Method

Another object of the present invention is a method for preparing a composition according to the invention, comprising:

- mixing the plasticisers with water, and optionally with the emulsifying and/or film-forming agents,
- adding starch under stirring until a gel forms,
- optionally adding a gelling agent,
- optionally adding a colouring agent,
- optionally adjusting the pH.

According to one embodiment, mixing the plasticisers with water, and optionally with the emulsifying and/or film-forming agents, is operated at ambient temperature, or hot, for example at a temperature between 60 and 95 °C.

Make-Up Method for Keratinous Materials

The present invention also relates to a make-up or care method for keratinous materials, in particular for the skin, eyelashes, eyebrows or lips, consisting of applying on said keratinous materials, in particular the skin, the eyelashes, the eyebrows or the lips, a composition according to the invention.

BRIEF DESCRIPTION OF THE DRAWINGS

FIG. 1

FIG. 1 compares the sweat resistance of a film obtained from a composition according to the invention (Example 1), and from a comparative composition that does not comprise the gelling agent of the invention.

EXAMPLES

Example 1: Eyeshadow

An eyeshadow is prepared having the composition presented in the following Table 1:

TABLE 1

| INCI name | Content (% by weight) |
|---|---|
| PRE-GELATINISED PEA STARCH (LYCOAT RS 720 FROM THE COMPANY ROQUETTE FRÈRES) | 23.5 |

TABLE 1-continued

| INCI name | Content (% by weight) |
|---|---|
| GLYCERIN | 10 |
| SORBITOL & WATER (70% MA) | 3.5 |
| PENTYLENE GLYCOL | 2.5 |
| ETHYL ALCOHOL | 5 |
| SCLEROTIUM GUM & XANTHAN GUM (ACTIGUM VSX 20) | 0.6 |
| POLYSORBATE 20 | 0.5 |
| COLOURING AGENTS | 10 |
| DEMINERALISED WATER | QSP |
| PRESERVATIVE | 0.5 |
| L-ARGININE | 0.06 |

The eyeshadow is prepared according to the following protocol:

- weigh the aqueous phase comprising water, glycerin, sorbitol, pentylene glycol, preservative and polysorbate 20 and stir in a rotor stator at 245 rpm,
- add the LYCOAT RS 720 while stirring, maintain the stirring for 5 min at 245 rpm once the gel has formed,
- add the Actigum VSX 20 while stirring in a rotor stator at 245 rpm,
- add the colouring agents while stirring in a rotor stator at 245 rpm,
- adjust the pH by adding arginine.

Upon application, the formula slides on the eyelid very well and its deposition is thicker than the eyeshadows on the market. The product does not crumble, and therefore does not deposit residues under the eye (on the cheekbone). The make-up result is intense, lasting over time. The film obtained is sweat and sebum resistant. It is peelable which enables easy make-up removal.

Example 2: Eyeshadow

An eyeshadow is prepared having the composition presented in Table 1 of Example 1, wherein the pre-gelatinised pea starch LYCOAT RS 720 from the company Roquette Freres has been substituted by a non-pre-gelatinised pea starch LYCOAT NG 720 from the company Roquette Freres.

The eyeshadow has been prepared according to the following protocol:

- weigh the aqueous phase comprising water, glycerin, sorbitol, pentylene glycol, preservative and polysorbate 20 and heat it to 85 °C while stirring in a rotor stator at 245 rpm,
- add the LYCOAT NG 720 while stirring, maintain the stirring for 5 min at 245 rpm once the gel has formed,
- add the Actigum VSX 20 while stirring in a rotor stator at 245 rpm,
- add the colouring agents while stirring in a rotor stator at 245 rpm,
- leave the formula to cool while Rayneri stirring until ambient temperature,
- adjust the pH by adding arginine.

Example 3: Resistance to Sweat and to Sebum

It was tested the resistance to sweat and to sebum of a film obtained from a composition according to Example 1, and from a comparative composition corresponding to the formula of Example 1, wherein the Actigum VSX 20 was removed.

For this test, product films of 250 μm were pulled with an automatic spreader over a 120 μm PET film. The film was left to dry for 24 h at ambient temperature then a drop of artificial sweat and a drop of phytosqualane (main component of sebum) was applied.

The results are presented in FIG. 1. Photo 1 corresponds to the film obtained by means of the eyeshadow of Example 1 according to the invention. No migration of the eyeshadow is observed in the drops of sweat or sebum, resulting in an excellent resistance to sweat and to sebum. Photo 2 corresponds to the comparative eyeshadow. Migration of the eyeshadow is observed in the drops of sweat, resulting in a lower resistance to sweat.

The invention claimed is:

1. A cosmetic composition comprising, in a continuous aqueous phase:
- at least one leguminous starch having an amylose content greater than or equal to 30%,
- at least one plasticiser selected from polyols,
- at least one hydrophilic gelling agent selected from xanthan gum, sclerotium gum, and the mixture thereof,
- an emulsifying agent, wherein the emulsifying agent has an HLB value between 8 and 20 and is selected from the group consisting of fatty acid esters, oxyethylene and/or oxypropylene sorbitol ethers, lysophospholipids, emulsifying waxes, and mixtures thereof, and
- water,
- wherein the cosmetic composition forms a sweat and sebum-resistant film for long-lasting, non-transferable makeup.

2. The composition according to claim 1, wherein the starch has a Brookfield viscosity in aqueous dispersion at 25 °C with 20% of dry matter between 10 and 10,000 mPa·s.

3. The composition according to claim 1, wherein the at least one leguminous starch has an amylose content that ranges from 30% to 75%.

4. The composition according to claim 1, wherein the leguminous starch is selected from pea starches.

5. The composition according to claim 1, wherein the starch is a hydrolysed and hydroxypropylated leguminous starch.

6. The composition according to claim 1, wherein the starch is present in a dry matter content between 1% and 25% by weight, in relation to the total weight of the composition.

7. The composition according to claim 1, wherein the polyols are selected from propylene glycol, butylene glycol, pentylene glycol, pentanediol, isoprene glycol, neopentyl glycol, glycerol, polyethylene glycols (PEG) having from 4 to 8 ethylene glycol units and/or sorbitol.

8. The composition according to claim 1, wherein the polyols are present in a content ranging from 10 to 20% by weight, in relation to the total weight of the composition.

9. The composition according to claim 1, wherein the composition comprises 25 to 65% by weight of water, in relation to the total weight of the composition.

10. The composition according to claim 1, wherein the hydrophilic gelling agent is selected from xanthan gum and a mixture of xanthan gum and of sclerotium gum in a weight ratio between 1:2 to 2:1.

11. The composition according to claim 1, further comprising at least one monoalcohol having from 1 to 5 carbon atoms.

12. The composition according to claim 1, further comprising a colouring agent selected from pigments and/or nacres.

13. The composition according to claim 1, wherein the emulsifying waxes are selected from the group consisting of self-emulsifying waxes, hydrolysed waxes, and mixtures thereof.

* * * * *